(12) United States Patent
Sebti et al.

(10) Patent No.: US 8,153,596 B2
(45) Date of Patent: *Apr. 10, 2012

(54) USE OF SH2 STAT3/STAT1 PEPTIDOMIMETICS AS ANTICANCER DRUGS

(75) Inventors: Said M. Sebti, Tampa, FL (US); Andrew D. Hamilton, Guilford, CT (US); James Turkson, Orlando, FL (US); Richard Jove, Glendora, CA (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 232 days.

This patent is subject to a terminal disclaimer.

(21) Appl. No.: 12/480,376

(22) Filed: Jun. 8, 2009

(65) Prior Publication Data

US 2009/0318367 A1    Dec. 24, 2009

Related U.S. Application Data

(63) Continuation of application No. PCT/US2007/086779, filed on Dec. 7, 2007.

(60) Provisional application No. 60/869,015, filed on Dec. 7, 2006.

(51) Int. Cl.
*A61K 38/06* (2006.01)
*C07K 5/08* (2006.01)
*C12N 5/00* (2006.01)

(52) U.S. Cl. .................. 514/21.2; 435/375; 530/331

(58) Field of Classification Search .................. None
See application file for complete search history.

(56) References Cited

U.S. PATENT DOCUMENTS 7,342,095 B2    3/2008   Turkson

*Primary Examiner* — Kamal Saeed
(74) *Attorney, Agent, or Firm* — Robert Varkonyi; Anton J. Hopen; Smith & Hopen, P.A.

(57) ABSTRACT

The subject invention concerns compositions and methods for blocking cancer cell growth or proliferation and/or inducing cancer cell death. Compositions of the present invention are peptidomimetics that inhibit STAT function. Peptidomimetics of the invention display selective inhibition of specific STAT isoform homo-dimerization. The peptidomimetic probes of STAT1 function, described herein, provide the means to preferentially inhibit STAT1 over STAT3 through the exploration of the C-terminus.

8 Claims, 3 Drawing Sheets

ISS610

ISS840

USE OF SH2 STAT3/STAT1 PEPTIDOMIMETICS AS ANTICANCER DRUGS

CROSS REFERENCE TO RELATED APPLICATIONS

This application is a continuation of prior filed International Application, Ser. No. PCT/US2007/086779 filed Dec. 7, 2007, which claims priority to U.S. provisional patent application No. 60/869,015 filed Dec. 7, 2006 which is hereby incorporated by reference into this disclosure.

STATEMENT OF GOVERNMENT INTEREST

This invention was made with government support under Grant No. CA78038 and CA55652 awarded by the National Cancer Institute. The government has certain rights in the invention.

FIELD OF INVENTION

This invention relates to materials and methods for blocking tumor growth and inducing tumor cell death by disrupting the activity of a STAT transcription factor protein, such as Stat3 and/or STAT1.

BACKGROUND OF THE INVENTION

Selective binding to closely related protein isoforms represents a particularly challenging problem in the search for molecules that might control cell signaling. This is nowhere more true than in the disruption of constitutively activated Signal Transducer Activators of Transcription (STAT) proteins as a viable anti-cancer therapy. Constitutive activation in numerous cancers, including leukemia and lymphomas, has provided evidence of a relationship between aberrant STAT activation and oncogenesis. As a result, the emerging significance of STAT signaling in the development of human cancers makes it an excellent target for new therapeutic intervention.

The STATs are a family of cytoplasmic proteins important in cell proliferation, differentiation, apoptosis and survival. STAT activated dimers have been shown to interact with specific promoter regulatory elements to induce target gene transcription. STATs are triggered through extracellular cytokine and growth factor stimulation resulting in receptor dimerization and activation. Phosphorylation of a crucial tyrosine residue provides binding sites for the recruitment of monomeric, non-phosphorylated STAT proteins via their Src homology 2 (SH2) domain. Receptor-bound STAT3 is then tyrosine phosphorylated by receptor and/or nonreceptor tyrosine kinases such as Src and JAK. Phosphorylated STAT proteins are then released from the receptor, and dimerization occurs through reciprocal phosphotyrosine-SH2 interaction. STAT dimers immediately translocate to the nucleus and bind with promoter regulatory elements. In normal functioning cells STAT activation is transitory and tightly regulated. However, aberrant STAT activation leads to the up-regulation of oncogenic pathways through dysregulated growth, suppression, angiogenesis and survival. The alleviation of irregular STAT signaling through dimerization inhibition provides a focused target for molecular intervention. Suppression of homo and hetero-dimerization through specific peptide sequences interacting with STAT has served to establish the structural attributes required for SH2 domain-inhibitor complementarity and further development of anti-cancer agents. Critical for their roles in cell biology the seven individual isoforms of STAT exhibit different functional properties. For example, STAT1 deficient mice display an impaired response to interferons, are susceptible to viral or bacterial pathogens and spontaneously develop tumors. Also, constitutively activated STAT1 signaling is present in a number of human cancers although its role in oncogenic pathways has yet to be fully elucidated. In contrast to STAT1, inhibition of persistant STAT3 activation by blocking tyrosine kinase activity has been repeatedly associated with tumor selective growth suppression and cell death.

It has been previously reported that the synthesis of STAT3 homodimerization inhibitors through the use of the peptide PY*LKTK (Y*=phosphotyrosine), which corresponds to the core of the native C-terminal STAT3 SH2 domain binding sequence GSAAPY*LKTKFIC. (see Turkson, J., Ryan, D., Kim, J. S., Zhang, Yi, Chen, Z., Haura, E., Laudano, A., Sebti, S., Hamilton, A. D., Jove, R., J. Bio. Chem., 2001, 276, 45443; Turkson, J., Kim, J. S., Zhang, S., Yuan, J., Huang, M., Glenn, M., Haura, E., Sebti, S., Hamilton, A. D., Jove, R., Mol. Canc. Therap., 2004, 3, 261; and Becker, S., Groner, B., Muller, C. W., Nature, 1998, 394, 145; which are incorporated herein by reference). Further optimization through the synthesis of a focused tripeptide library identified the importance of the central Y*L residues for inhibitory activity. Specific STAT selectivity was associated with functional group substitution of the peptide termini. The native binding sequence from STAT1 (PKGTGY*IKTELIS) shows marked variation from that of STAT3 near the termini of the region investigated, corresponding well with the selectivities observed among prepared compounds. By testing with a range of substituents of varying polarity, size and orientation it was shown that a phenyl nitrile substituent at the western Y* N-terminus as being crucial in the series for enhanced inhibition of STAT3 dimerization.

SUMMARY OF INVENTION

Here, the invention includes a comprehensive series of phosphopeptidomimetic probes that display selective inhibition of specific STAT isoform homo-dimerization. The peptidomimetic probes of STAT1 function, described herein, provide the means to preferentially inhibit STAT1 over STAT3 through the exploration of the C-terminus. Improved activity and selectivity was achieved through a combination of exploratory genetic optimization for ligand docking (GOLD), quantitative structural activity relationship (QSAR) modeling and a comprehensive synthetic program. Evaluation was carried out through pre-incubation of specific concentrations of peptidomimetics with nuclear extracts containing STAT1 and STAT3 for 30 minutes at room temperature before incubation with radiolabeled hSIE oligonucleotide probes and ESMA analysis. Standard peptide synthetic procedures using HBTU and DIPEA were employed to furnish the library of functionalized inhibitors.

BRIEF DESCRIPTION OF THE DRAWINGS

For a fuller understanding of the invention, reference should be made to the following detailed description, taken in connection with the accompanying drawings, in which.

Residue numbers refer to the corresponding residues of unphosphorylated STAT1 (homo sapiens) (pdb: 1YVL8).

Figure 2A:
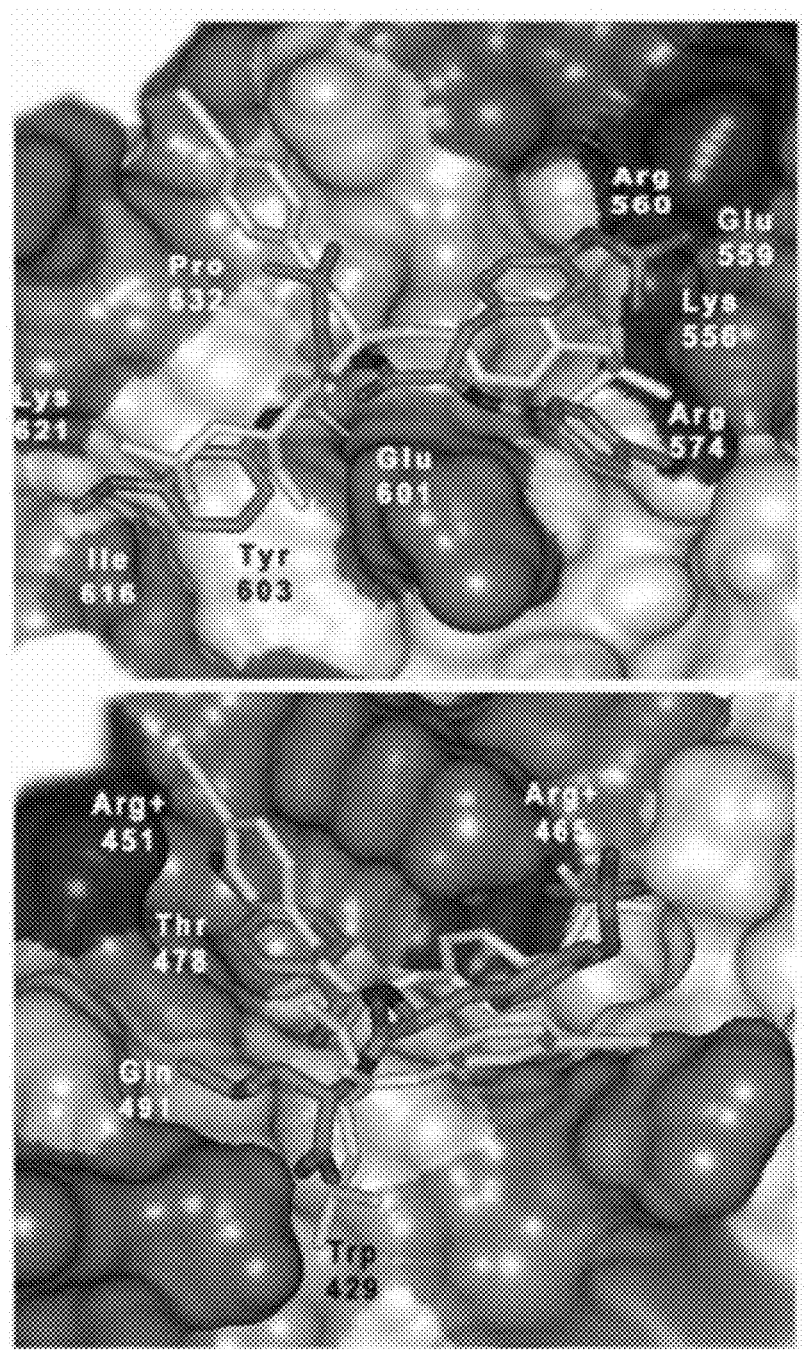
FIG. 2A describes comparitive GOLD (Genetically Optimized Ligand Docking) docking of ISS840 (green) and JSK610 (yellow) within the SH2 domain of STAT1 protein.
Figure 2B:
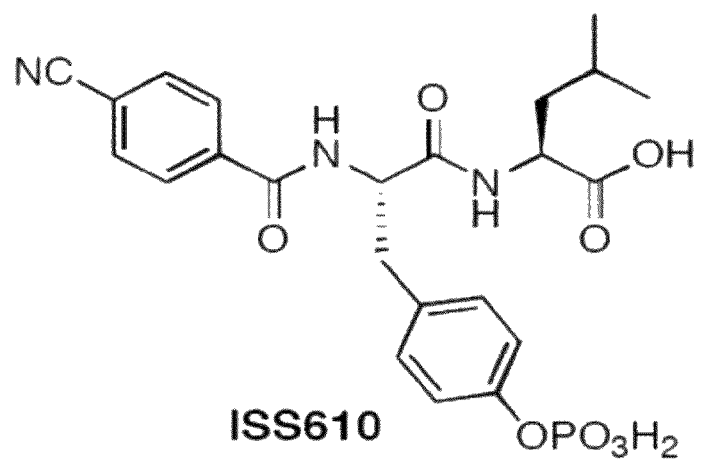
Figure 2B:
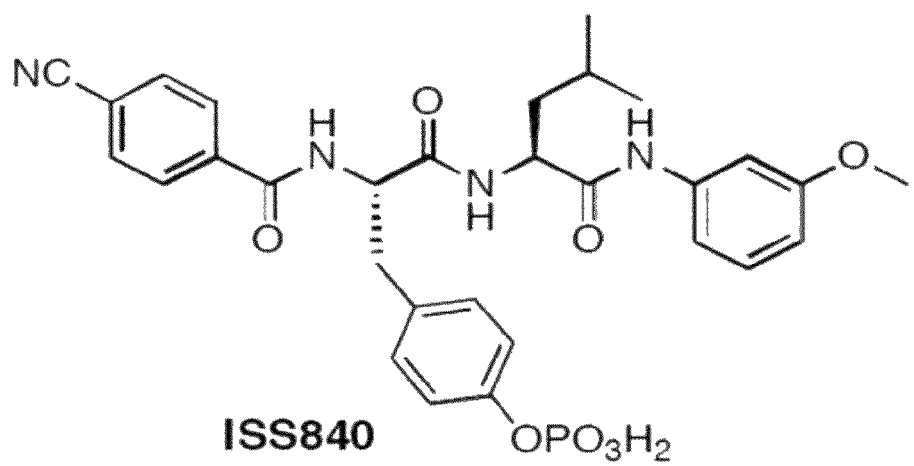

FIG. 2B describes comparitive GOLD docking of ISS840 (yellow) and ISS610 (green) within the SH2 domain of STAT3 protein. Residue numbers refer to the corresponding residues of STAT3β homodimer bound to DNA (Mus musculus) (pdb: 1BG19). (red hydrophobic to blue hydrophilic).

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The subject invention concerns compositions for blocking cancer cell growth or proliferation and/or inducing cancer cell death. Compositions of the invention comprise peptidomimetic molecules that are inhibitors of STAT proteins. Peptidomimetics within the scope of the invention include peptidomimetics having the structure R—Y*L, where R is a functional group projected from the Eastern terminal.

In one embodiment, a peptidomimetic of the invention has the structure shown in formula I:

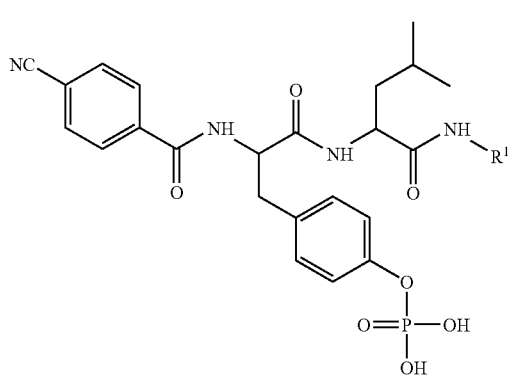

Figure 1:
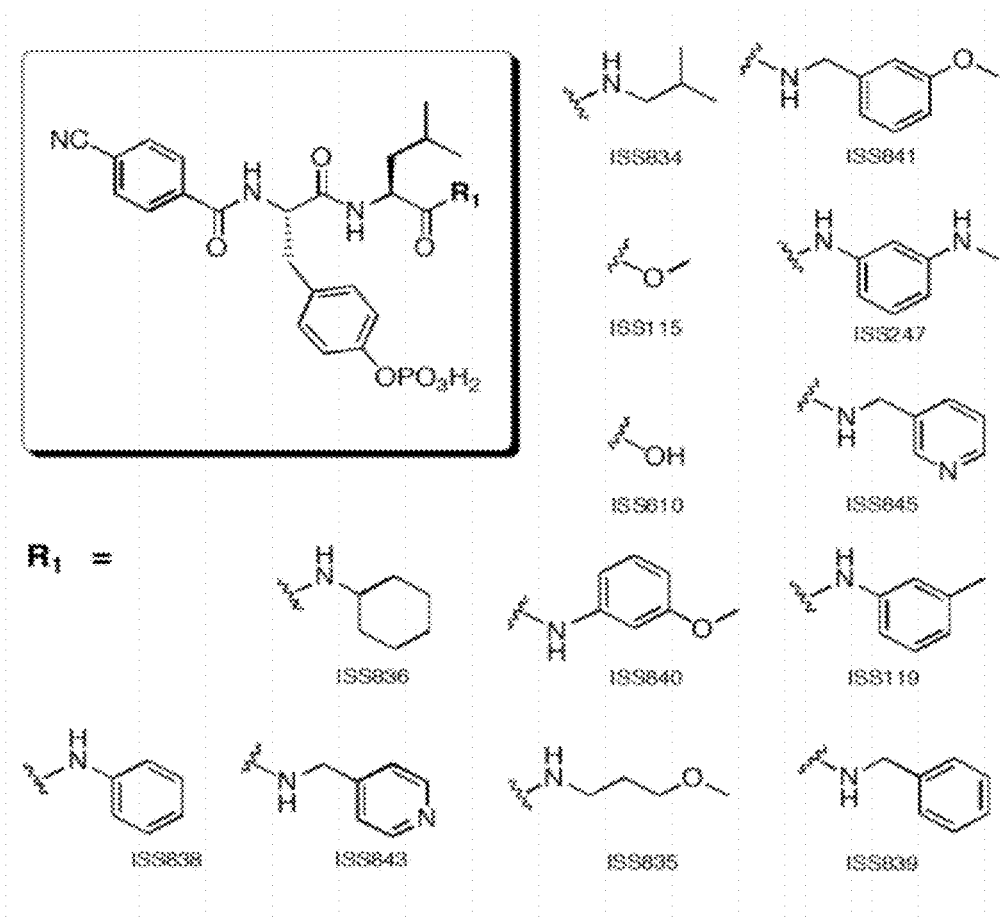
FIG. 1 shows a peptidomimetic library; substitution of central (4-phenyl nitrile)Y*L core with a range of functional groups projected from the Eastern terminal.

(I)

Wherein is R1 alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO2, —NH2, —N-alkyl, alkyl including —CH3, alkoxy including —OCH3, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; or a salt thereof. In a preferred embodiment, peptidomimetics of the invention have an R1 group selected from alkyl, phenyl, pyridyl, alkoxy and cyclohexyl moieties. Structure of the R groups in preferred embodiments of peptidomimetics having the structure shown in formula I are shown in FIG. 1.

As used herein, alkyl means straight or branched chain, saturated or mono- or polyunsaturated hydrocarbon groups having from 1 to 20 carbon atoms and C1-X alkyl means straight or branched chain alkyl groups containing from one up to X carbon atoms wherein X is any positive integer. For example, C1-6 alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O-group in which the aryl group is as described herein. Alkylcarbonyl means a RC(O)-group where R is an alkyl group as previously described. Alkoxycarbonyl means an ROC(O)-group where R is an alkyl group as previously described. Cycloalkylcarbonyl means an RC(O)-group where R is a cycloalkyl group as previously described. Cycloalkoxycarbonyl means an ROC(O)-group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO-group in which the heterocycloalkyl group is as described herein. Aryloxycarbonyl means an ROC(O)-group where R is an aryl group as previously described. Heteroaryloxycarbonyl means an ROC(O)-group where R is a heteroaryl group as previously described. Heterocycloalkoxy means a heterocycloalkyl-O-group in which the heterocycloalkyl group is as previously described. Heterocycloalkoxycarbonyl means an ROC(O)-group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, benzyl, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, isoxazolyl, thiazolyl, pyrazolyl, pyridyl, pyrimidyl, purinyl, indolyl, quinolinyl, isoquinolinyl, benzoquinolinyl, carbazolyl, and diazaphenanthrenyl.

The subject invention also concerns compositions comprising a peptidomimetic of the invention, or a salt thereof, in a pharmaceutically acceptable carrier or diluent. Examples of peptidomimetics of the invention are shown in Table 1 and have been designated with an "ISS" number. Peptidomimetics of the invention, such as those exemplified herein are potent, and selective disrupters of active Stat1 and provides the ability to preferentially inhibit STAT1 over STAT3. Shown in Table 1 is the lowest energy GOLD docked conformation of peptidomimetics ISS 840 in the SH2 domain of Stat1.

Salts of the peptidomimetics of the invention include those which are prepared with acids or bases, depending on the particular substituents present on the subject peptidomimetics described herein. Examples of a base addition salts include sodium, potassium, calcium, ammonium, or magnesium salt. Examples of acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Salts of platinum complexes of the invention can be prepared using conventional techniques.

Peptides of the invention can be readily prepared using standard techniques known in the art, including chemical synthesis (Merrifield, 1963) and genetic engineering. Peptidomimetics of the invention can be synthesized or prepared from peptides using standard chemical procedures and materials.

Peptidomimetics having substitution of amino acids other than those specifically exemplified in the subject peptidomimetics are also contemplated within the scope of the present invention. For example, non-natural amino acids can be substituted for the amino acids of a peptidomimetic of the invention, so long as the peptidomimetic having substituted amino acid(s) retains substantially the same activity as the peptidomimetic in which amino acid(s) have not been substituted. Examples of non-natural amino acids include, but are not limited to, omithine, citrulline, hydroxyproline, homoserine, phenylglycine, taurine, iodotyrosine, 2,4-diaminobutyric acid, .alpha.-amino isobutyric acid, 4-aminobutyric acid, 2-amino butyric acid, .gamma.-amino butyric acid, .epsilon.-amino hexanoic acid, 6-amino hexanoic acid, 2-amino isobutyric acid, 3-amino propionic acid, norleucine, norvaline, sarcosine, homocitrulline, cysteic acid, .tau.-butylglycine, .tau.-butylalanine, phenylglycine, cyclohexylalanine, .beta.-alanine, fluoro-amino acids, designer amino acids such as .beta.-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Conservative substitutions whereby a peptidomimetic having an amino acid of one class (i.e. non-polar, uncharged polar, basic, and acidic) is replaced with another amino acid of the same class fall within the scope of the subject invention so long as the peptidomimetic having the substitution still retains substantially the same biological activity as a peptidomimetic that does not have the substitution. Thus, peptidomimetics of the invention having the structure R1*L (wherein R.sup.1 is as defined herein) include those where the leucine (L) residue is replaced with a nonpolar amino acid, such as valine, alanine, etc. Also specifically contemplated within the scope of the invention are compounds of formula R1Y*L having analogs of Y* or L wherein the peptidomimetic having the analog has substantially the same biologically activity as a non-analog peptidomimetic. For example, analogs of Y* include those where the aromatic ring of phosphotyrosine can be substituted with various substituents including, but not limited to, any halogen, —OH, —NO2, —NH2, —COOH, alkyl(such as —CH3), and alkoxy (such as —OCH3).

The subject invention also concerns methods for inhibiting the growth or replication of a cell having abnormal growth or replication or whose growth or replication is uncontrolled, such as a cancer cell. In one embodiment, methods of the invention comprise inhibiting function of a STAT by contacting a cell expressing a STAT with a peptidomimetic of the invention wherein the peptidomimetic is taken in or otherwise provided inside the cell. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Methods of the invention also comprise inhibiting the function and/or growth and replication of a cell that is aberrantly or constitutively expressing a STAT, and selectively inhibiting a given STAT isoform over another, such as Stat1 over Stat3. In one embodiment, the method comprises contacting a cell with a peptidomimetic of the invention. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

While peptidomimetics described herein are generally more selective for Stat1 over Stat3, the selectivity of these peptidomimetics may be influenced by the presence and the type, as well as the positioning, of functional groups on the aromatic ring.

The subject invention also concerns methods for inducing apoptosis in a target cell. In one embodiment, the method comprises contacting a cell with a peptidomimetic of the invention. In one embodiment, the cell is a tumor cell, cancer cell, or a transformed cell. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Peptidomimetics of the invention can be delivered to a cell either through direct contact with the cell or via a carrier means. Carrier means for delivering compositions to cells are known in the art and include encapsulating the composition in a liposome moiety, and attaching the platinum complexes to a protein or nucleic acid that is targeted for delivery to the target cell. Published U.S. patent application Nos. 20030032594 and 20020120100 disclose amino acid sequences that can be coupled to a composition and that allows the composition to be translocated across biological membranes. Published U.S. patent application No. 20020035243 also describes compositions for transporting biological moieties across cell membranes for intracellular delivery.

The subject invention also concerns methods for treating tumors and oncological disorders in a patient. In one embodiment, an effective amount of a peptidomimetic of the present invention is administered to a patient having an oncological disorder and who is in need of treatment thereof. The patient can be a human or other mammal, such as a primate (monkey, chimpanzee, ape, etc.), dog, cat, cow, pig, or horse, or other animals having an oncological disorder. Means for administering and formulating a peptidomimetic for administration to a patient are known in the art, examples of which are described herein. Oncological disorders that can be treated using the subject invention include cancer and/or tumors of the breast, kidney, mouth, larynx, esophagus, stomach, testis, cervix, head, neck, colon, ovary, lung, bladder, skin, muscle, pancreas, prostate, bone, eye, blood cells, and brain. The peptidomimetics of the invention can also be used to treat other disorders that are associated with aberrant or constitutive expression of a STAT, such as Stat1 and/or Stat3.

For the treatment of tumors and oncological disorders, the peptidomimetics of this invention can be administered to a patient in need of treatment alone, or in combination with other antitumor or anticancer substances and/or with radiation therapy and/or with surgical treatment to remove a tumor or cancerous tissue. These other substances or radiation treatments may be given at the same or different times as the peptidomimetics of this invention. For example, the peptidomimetics of the present invention can be used in combination with mitotic inhibitors such as taxol or vinblastine, alkylating agents such as cisplatin, cyclophosamide or ifosfamide, antimetabolites such as 5-fluorouracil or hydroxyurea, DNA intercalators such as adriamycin or bleomycin, topoisomerase inhibitors such as etoposide or camptothecin, anti-angiogenic agents such as angiostatin, antiestrogens such as tamoxifen, and/or other drugs or antibodies that inhibit cancer cells, such as, for example, GLEEVEC (Novartis) and HERCEPTIN (Genetech), respectively.

Therapeutic application of the subject peptidomimetics, and compositions containing them, can be accomplished by any suitable therapeutic method and technique presently or prospectively known to those skilled in the art. The peptidomimetics can be administered by any suitable route known in the art including, for example, topical, oral, nasal, rectal, parenteral, subcutaneous, intramuscular, or intravenous routes of administration. Administration of the peptidomimetics of the invention can be continuous or at distinct intervals as can be readily determined by a person skilled in the art. The dosage to be administered to a patient can vary depending on several factors, including age, weight, and sex of the patient, and the type and severity of the disease. The ordinarily skilled clinician can determine suitable dosages following evaluation of the patient.

Compounds useful in the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive peptidomimetic is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptidomimetics of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptidomimetics based on the weight of the total composition including carrier or diluent.

The peptidomimetics and compositions of the subject invention can also be administered utilizing liposome technology, slow release capsules, implantable pumps, and biodegradable containers. These delivery methods can, advantageously, provide a uniform dosage over an extended period of time.

The subject peptidomimetics can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides are known in the art (see, for example, U.S. Pat. No. 4,179,337). The subject peptidomimetics can also be modified to improve cell membrane permeability. In one embodiment, cell membrane permeability can be improved by attaching a lipophilic moiety, such as a steroid, to the peptidomimetic. Other groups known in the art can be linked to peptidomimetics of the present invention.

Improved activity and selectivity was achieved through a combination of exploratory genetic optimization for ligand docking (GOLD), quantitive structural activity relationship (QSAR) modeling and a comprehensive synthetic program. Evaluation was carried out through pre-incubation of specific concentrations of peptidomimetics with nuclear extracts containing STAT1 and STAT3 for 30 minutes at room temperature before incubation with radiolabeled hSIE oligonucleotide probes and ESMA analysis. Standard peptide synthetic procedures using HBTU and DIPEA were employed to furnish the library of functionalized inhibitors.

TABLE 1

| | $IC_{50}$ values (μM) against STAT dimers | | |
|---|---|---|---|
| Inhibitor | STAT3:STAT3 $IC_{50}$ values, μM$^a$ | STAT1:STAT1 $IC_{50}$ values, μM$^a$ | STAT1v STAT3 |
| ISS610 | 42 | 310 | 1:7.4 |
| ISS834 | 760 | 21 | 36:1 |
| ISS835 | 210 | 620 | 1:3 |
| ISS836 | 605 | 25 | 24:1 |
| ISS838 | 380 | 310 | ~1:1 |
| ISS839 | 760 | 800 | ~1:1 |
| ISS840 | 560 | 1 | 400:1 |
| ISS841 | 250 | 58 | 4.3:1 |
| ISS843 | 405 | 90 | 4.5:1 |
| ISS845 | na | na | — |
| ISS119 | na | na | — |
| ISS115 | na | na | — |

Table 1 shows the selective disruption of STAT family members by peptidomimetics. Note: Nuclear extracts containing active STAT1 and STAT3 were preincubated with or without peptidomimetics for 30 min before incubation with radiolabeled hSIE probe and EMSA analysis. aValues are means of three experiments, standard deviation is given in parentheses (na=not active).

Variation of the electronic and steric properties of substituents at the Leu Eastern terminus was found to be critical for STAT1 and STAT3 isoform selectivity (Table 1). Optimized STAT3 isoform dimerization inhibition results were achieved through previously reported ISS610 (IC50 value of 42±23 μM), a monofunctionalized dipeptide. ISS610 was tested as a representative STAT3 selective peptidomimetic against constitutively active STAT3-dependant v-Src transformed fibroblasts and was found to suppress cell growth significantly. ref Modification of ISS610 via amide coupling to the free acid of the Leu residue was further found to reduce selectivity and activity toward STAT3 dimerization. For example, the addition of an isopropyl or cyclohexyl substituent results in a respective drop in affinity to 760 μM (ISS834) and 605 μM (ISS836) compared to 42 μM (ISS610). GOLD docking of ISS610 within the SH2 domain of STAT3 (FIG. 2B) was used to confirm the limited space available for scaffold extension.

Subsequent molecular docking of STAT3 peptidomimetic derivatives suggested that the location of the pendant phosphorylated tyrosine within a hydrophilic pocket (Arg) was conserved in all the peptidomimetic binding models. Control compounds synthesized without the phosphorylated Tyr lost all dimerization inhibitory activity toward STAT isoforms. The orientation of the peptide and subsequent projection of functionality is determined by the positioning of the phosphate in relation to the hydrophilic Arg cleft. Spatial constraints upon ISS610 limited the possibility of chain elongation; experimental results confirmed these model findings.

Suitable spatial arrangement of functional groups at the Leu carboxylic acid terminus was critical for STAT1 inhibition. Substitution with m-methoxyphenylaniline (ISS840) gave excellent STAT1 homo-dimerization inhibition (IC50 value of 1.4 μM), with little effect on STAT3:STAT3 dimer formation; (IC50 value of 560 μM). Selectivity of a lesser magnitude toward STAT1 was achieved with ISS834 (21 μM), 836 (25 μM), 841 (58 μM), and 843 (90 μM). STAT1 affinity appears to require projection of a hydrophobic group towards hydrophobic residues, Tyr 603 and Ile 616. STAT1 inhibitor development was achieved without the assistance of crystal structure docking models.

When developed with our library of STAT1 and STAT3 peptidomimetic inhibitors, a QSAR model showed crucial structural attributes necessary for isoform selectivity and affinity. PLS and genetic PLS (G/PLS) algorithms, as implemented within Cerius were used to model STAT1 and STAT3 inhibition agents. Focus was placed on specific descriptors, which were deemed pertinent to successful protein-protein interactions. The model indicated that increasing the number of hydrogen bond donors elevated STAT1 selectivity, whereas preferential STAT3 affinity was obtained through increased hydrogen bond acceptor sites. Isoform selectivity was also directly related to inhibitor size, which correlated well with the experimental findings; STAT1 inhibitors were larger in dimensions than the corresponding STAT3 agents.

Docking studies were performed on our lead STAT1 agents using coordinates from the unphosphorylated STAT1 crystal structure. ISS840 had excellent complementarity with the protein surface as shown in FIG. 2A. Phosphate incorporation into the Arg 560 cleft and projection of the benzyl nitrile toward Arg 574 provided a basis for its high affinity. Additional contacts appear to include hydrogen-bonding between the terminal methoxy group and Lys 621 which presumably stabilizes the C-terminal region of the peptidomimetic within the SH2 domain.

Accordingly, the inventors have demonstrated a peptidomimetic approach for the inhibition of STAT protein dimerization which can be extended to display selectivity toward specific STAT isoforms. Our multifaceted approach using GOLD and QSAR modeling is now being applied to a non-peptidomimetic scaffold to improve the membrane permeability of our agents while retaining the key structural attributes required for selectivity.

The disclosure of Turkson, et al., U.S. Application No. 2005/0004009A1 is expressly incorporated herein by reference in its entirety.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A peptidomimetic having the structure shown in formula I:

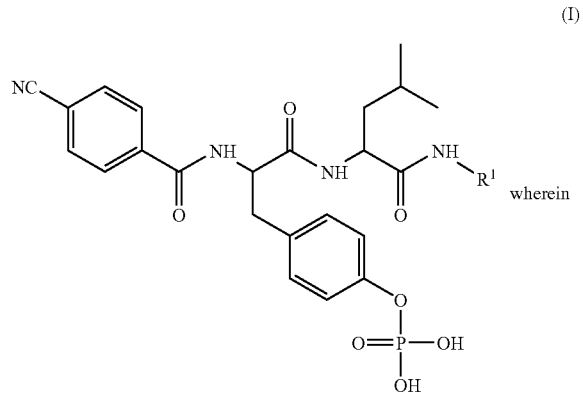

wherein $R^1$ is selected from the group consisting of —OH, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO$_2$, —NH$_2$, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, heterocycloalkoxycarbonyl, and a salt thereof.

2. The peptidomimetic according to claim 1, wherein R1 is selected from the group consisting of isopropyl and isobutyl.

3. The peptidomimetic according to claim 1, wherein R1 is $C_{1-4}$ alkoxy.

4. The peptidomimetic according to claim 1, wherein R1 is cyclohexyl.

5. The peptidomimetic according to claim 1, wherein R1 is phenyl optionally substituted with one or more halogen, —CN, —$NO_2$, —$NH_2$, —$CH_3$, —$NCH_3$ or —$OCH_3$.

6. The peptidomimetic according to claim 1, wherein R1 is benzyl optionally substituted with one or more halogen, —CN, —$NO_2$, —$NH_2$, —$CH_3$, or —$OCH_3$.

7. The peptidomimetic according to claim 1, wherein R1 is heteroaryl optionally substituted with one or more halogen, —CN, —$NO_2$, —$NH_2$, —$CH_3$, or —$OCH_3$.

8. The peptidomimetic according to claim 1, selected from the group consisting of:

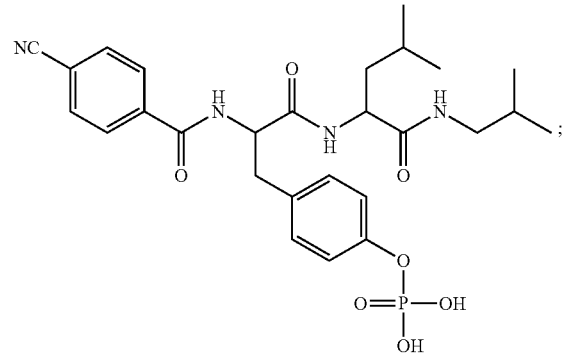

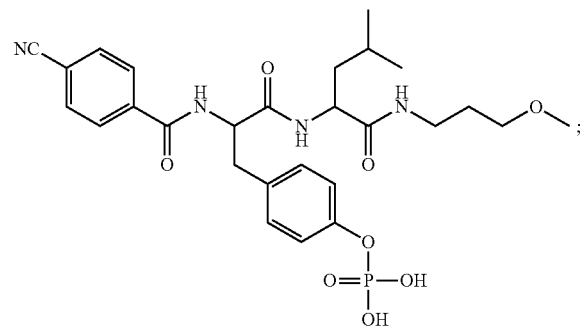

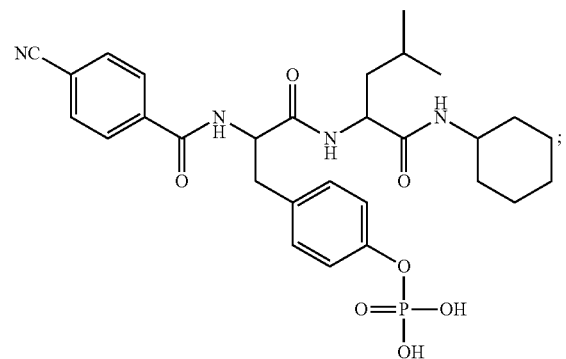

-continued

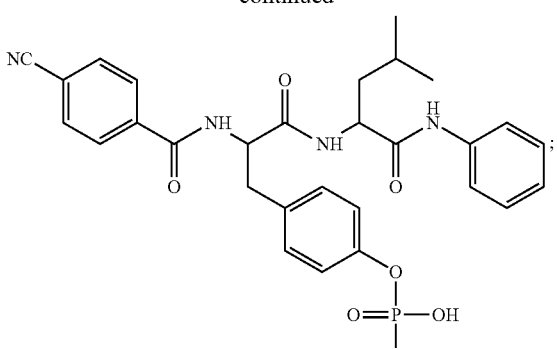

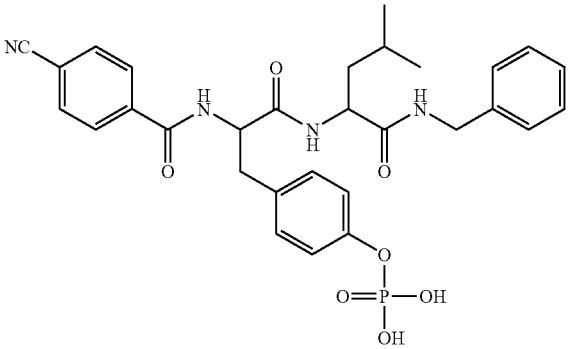

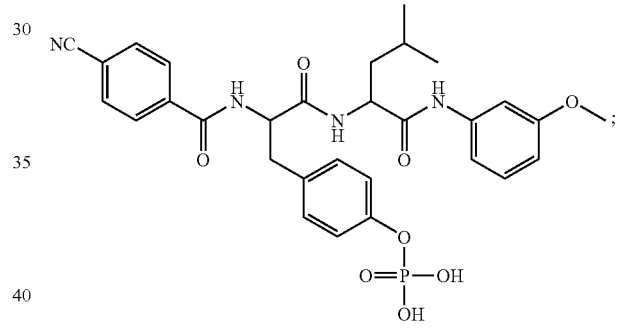

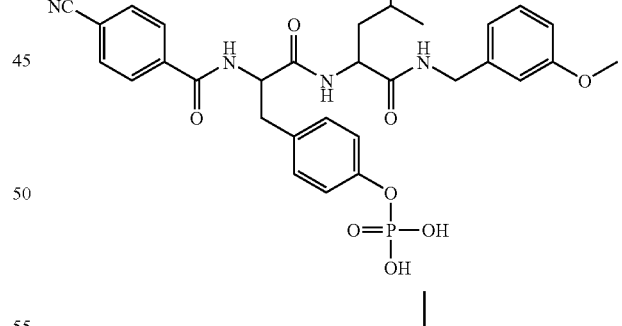

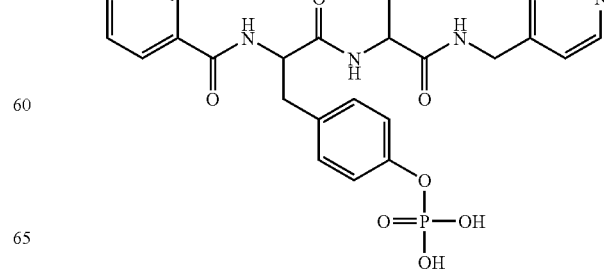

13
-continued
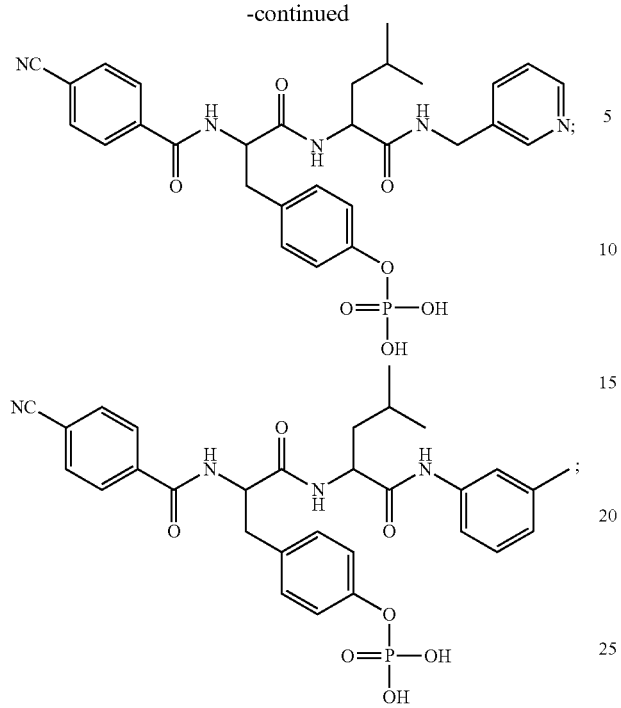
14
-continued
and
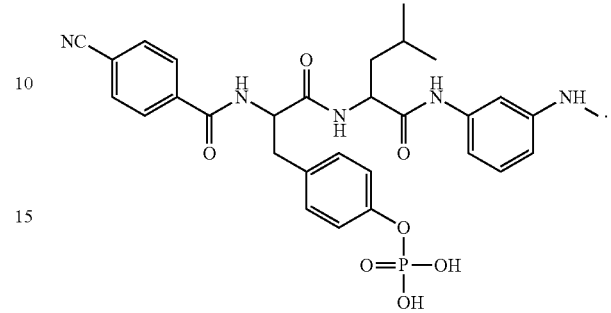
* * * * *